(12) United States Patent
Sinderby et al.

(10) Patent No.: US 6,901,286 B1
(45) Date of Patent: May 31, 2005

(54) METHOD AND SYSTEM FOR PRODUCING A HIGHER QUALITY ELECTROMYOGRAPHIC SIGNAL FROM AN ELECTRODE ARRAY

(75) Inventors: Christer Sinderby, Montreal (CA); Jennifer Beck, Montreal (CA); Lars Lindstrom, Moindal (SE)

(73) Assignee: Universite de Montreal, Montreal (CA)

( * ) Notice: Subject to any disclaimer, the term of this patent is extended or adjusted under 35 U.S.C. 154(b) by 301 days.

(21) Appl. No.: 10/030,366

(22) PCT Filed: Jul. 7, 2000

(86) PCT No.: PCT/CA00/00808
§ 371 (c)(1),
(2), (4) Date: Apr. 8, 2002

(87) PCT Pub. No.: WO01/03579
PCT Pub. Date: Jan. 18, 2001

(30) Foreign Application Priority Data
Jul. 7, 1999 (CA) .............................. 2276962

(51) Int. Cl.[7] ............................................ A61B 5/0488
(52) U.S. Cl. ...................................... 600/546; 600/407
(58) Field of Search ............................... 600/407, 424, 600/534, 536, 546

(56) References Cited

U.S. PATENT DOCUMENTS 5,505,208 A * 4/1996 Toomim et al. ............ 600/546
5,671,752 A   9/1997 Sinderby et al. ............ 128/733
6,280,395 B1 * 8/2001 Appel et al. ................ 600/546
6,366,813 B1 * 4/2002 DiLorenzo ................... 607/45

FOREIGN PATENT DOCUMENTS

WO   WO 98/48877   11/1998   .......... A61M/16/00
WO   WO 99/32032   * 7/1999   ......... A61B/5/0488

OTHER PUBLICATIONS

"The Position of Innervation Zones in the Biceps Brachii Investigated by Surface Electromyography", Tadashi Masuda et al., IEEE Transactions on Biomedical Engineering, vol. BME–32, No. 1, 1985.
"Spatial Filtering of Noninvasive Multielectrode EMG Part I–Introduction to Measuring Technique and Applications", Reucher et al., IEEE Transactions on Biomedical Engineering, vol. BME–34, No. 2, 1987.

* cited by examiner

Primary Examiner—Carl Layno
(74) Attorney, Agent, or Firm—Perman & Green, LLP

(57) ABSTRACT

A method and system for producing higher quality electromyogram (EMG) signals utilizes an array of electrodes for sensing a plurality of EMG signals in an electrically active region of a subject's muscle. A weighting function is applied to the EMG signals to produce weighted signals. This weighting function contains correction features for the relative locations of the center of the electrically active region and the electrodes. The quality of the weighted EMG signals is evaluated, and the weighted signals or sum or mean of the weighted signals whose evaluated quality is insufficient are replaced. A sum or mean of a feature of the weighted signals is calculated to produce a higher quality electromyocardiographic signal. The method and system can also be used to determine signal strength or frequency contents of a signal falling outside the array of electrodes.

28 Claims, 11 Drawing Sheets

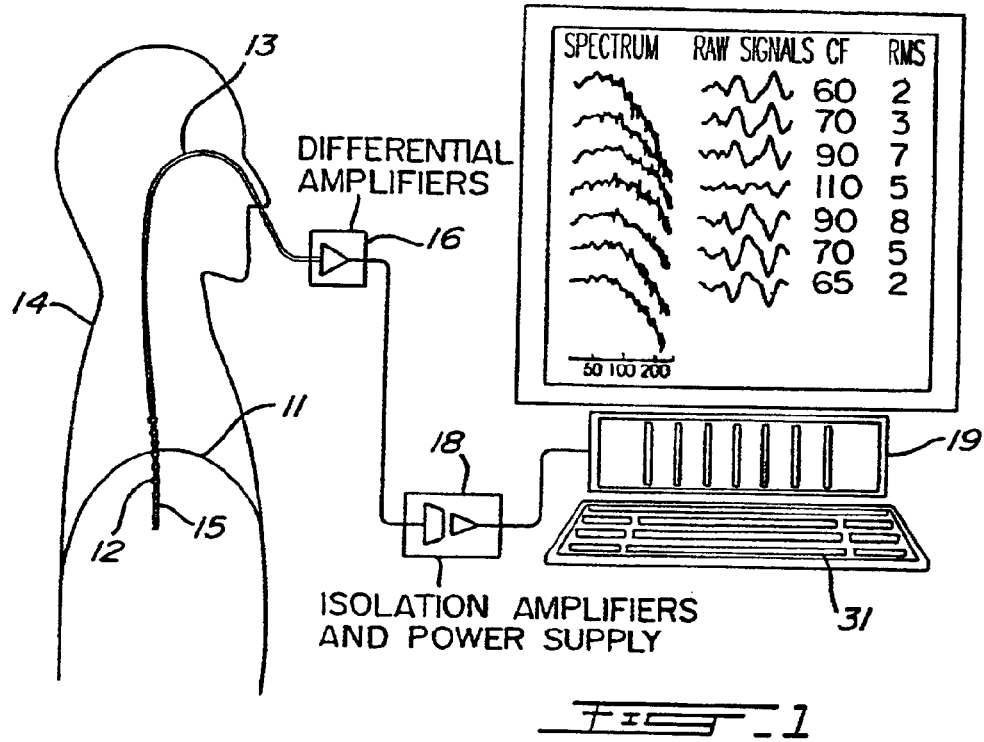
FIG_1
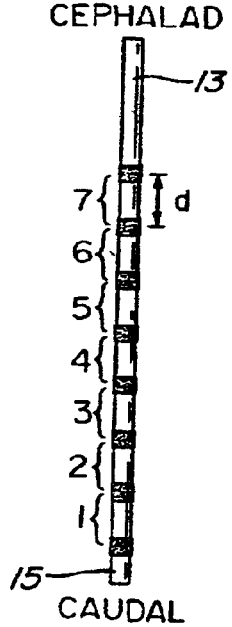
FIG_2

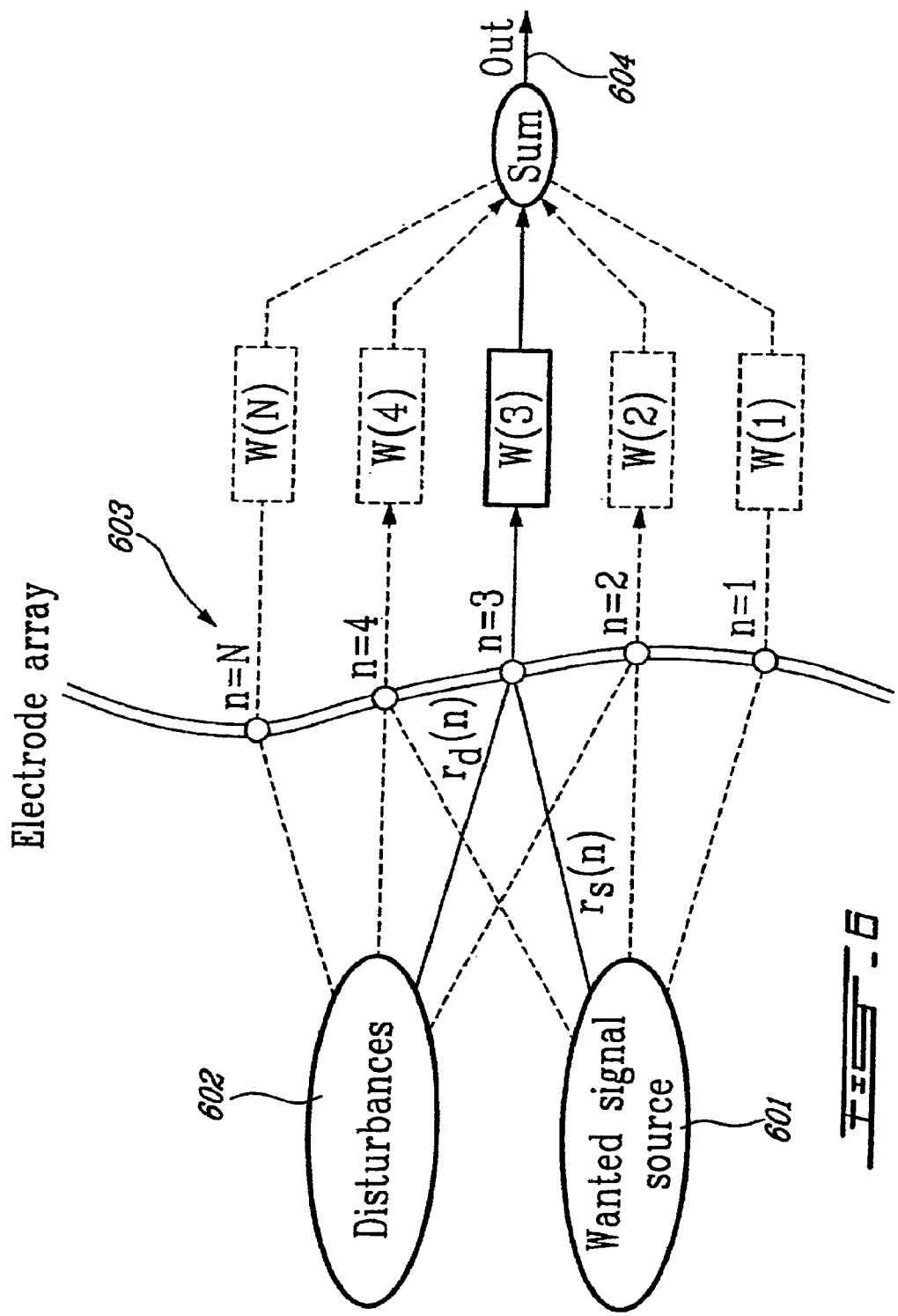

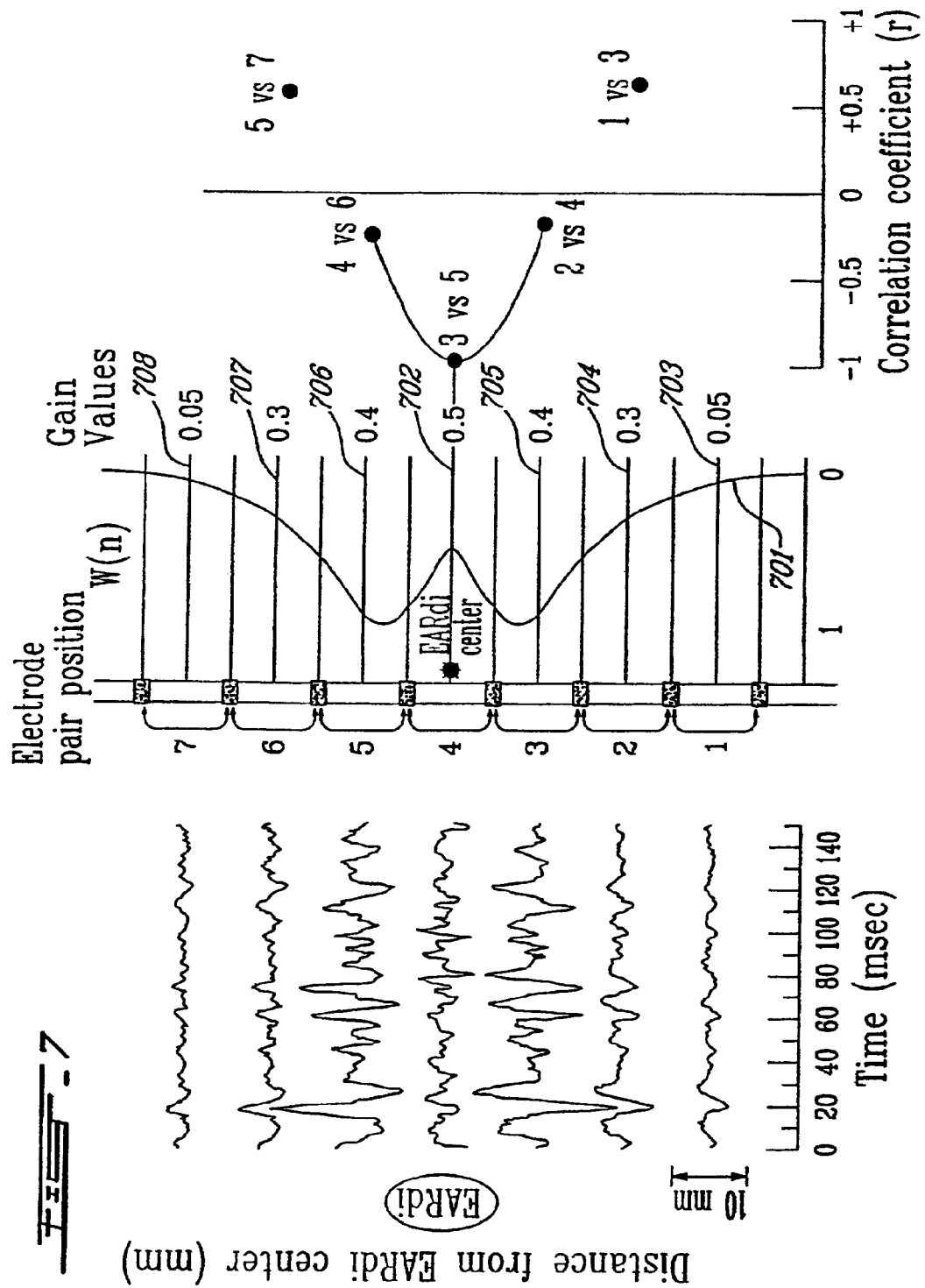

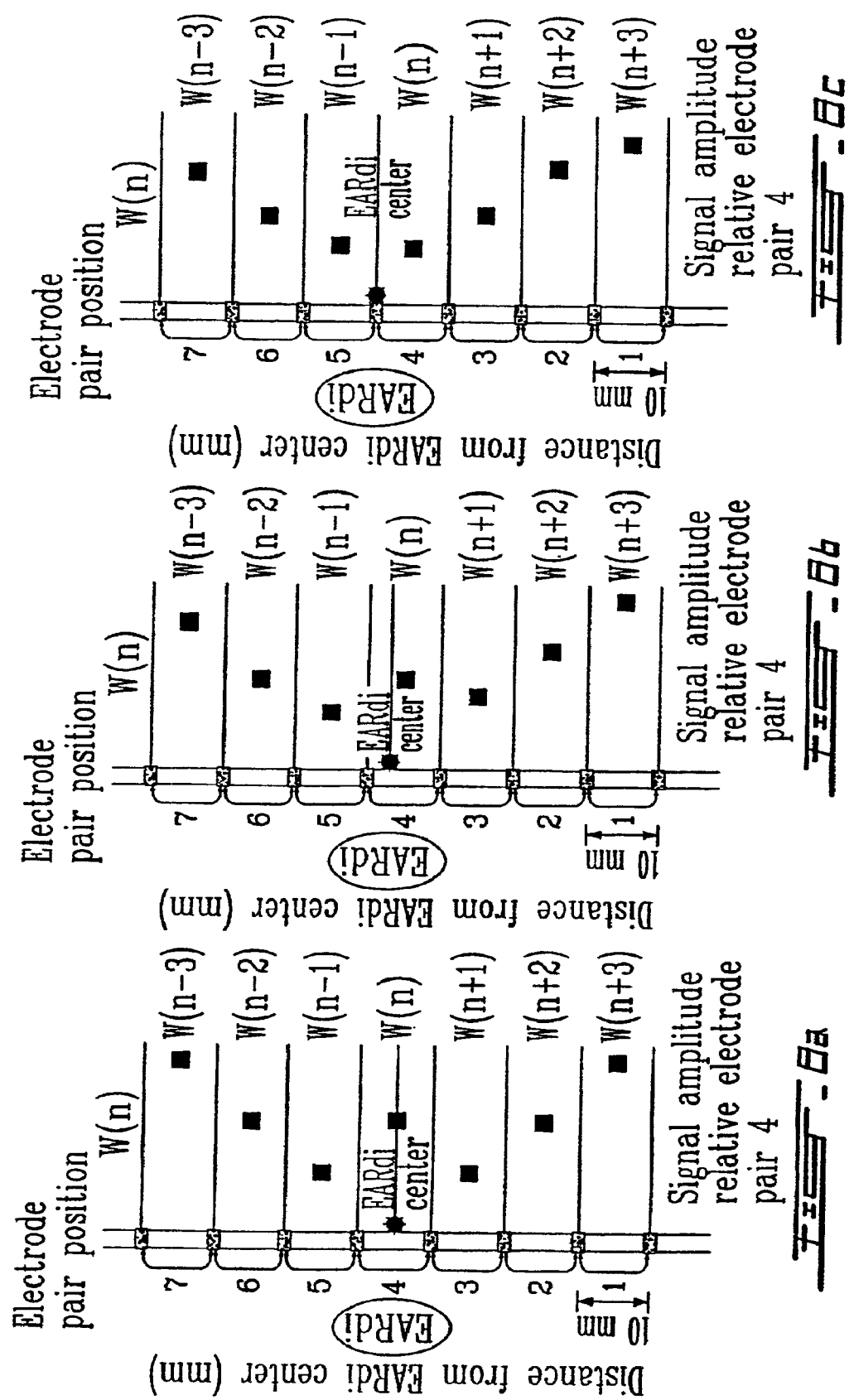

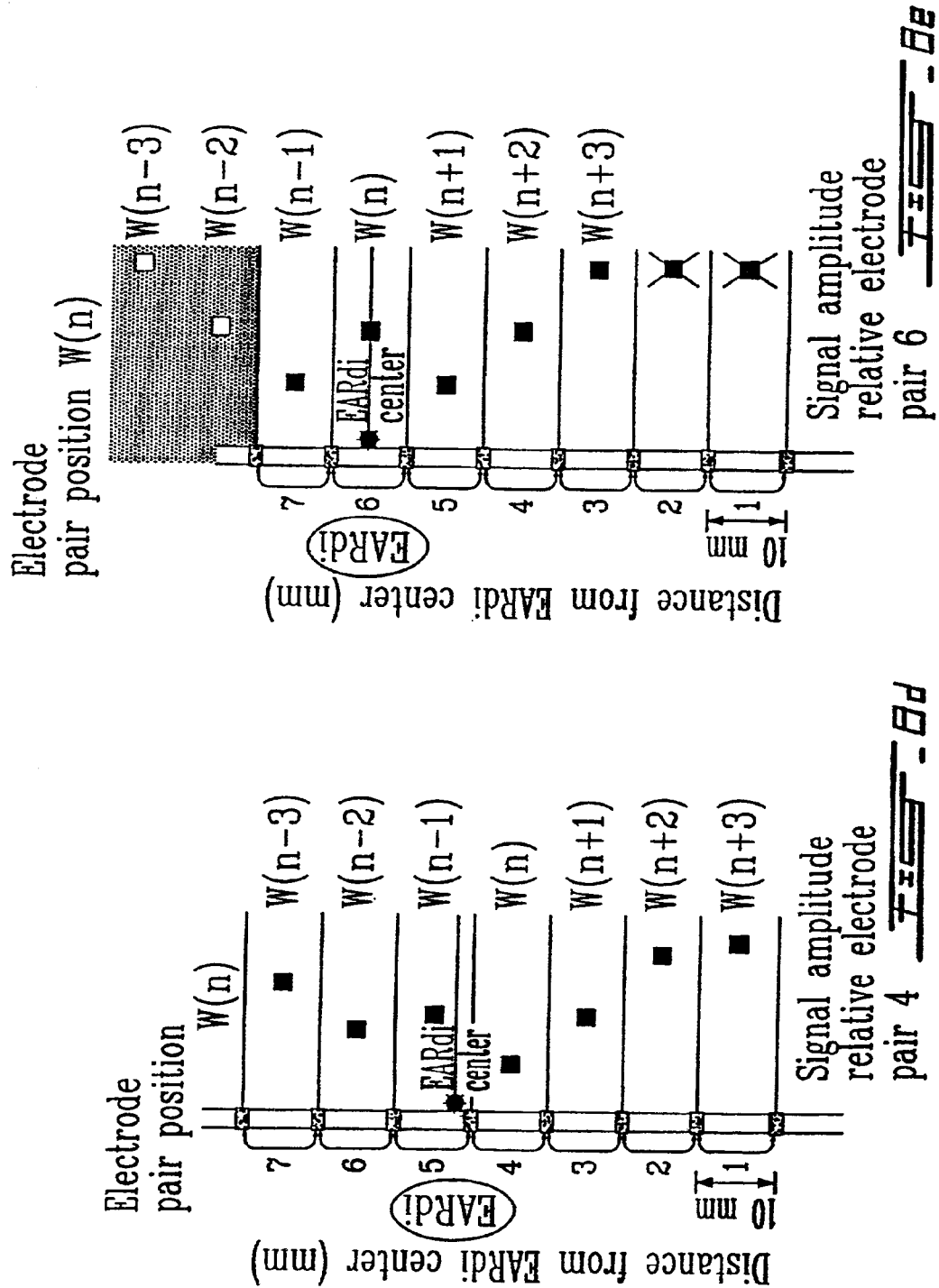

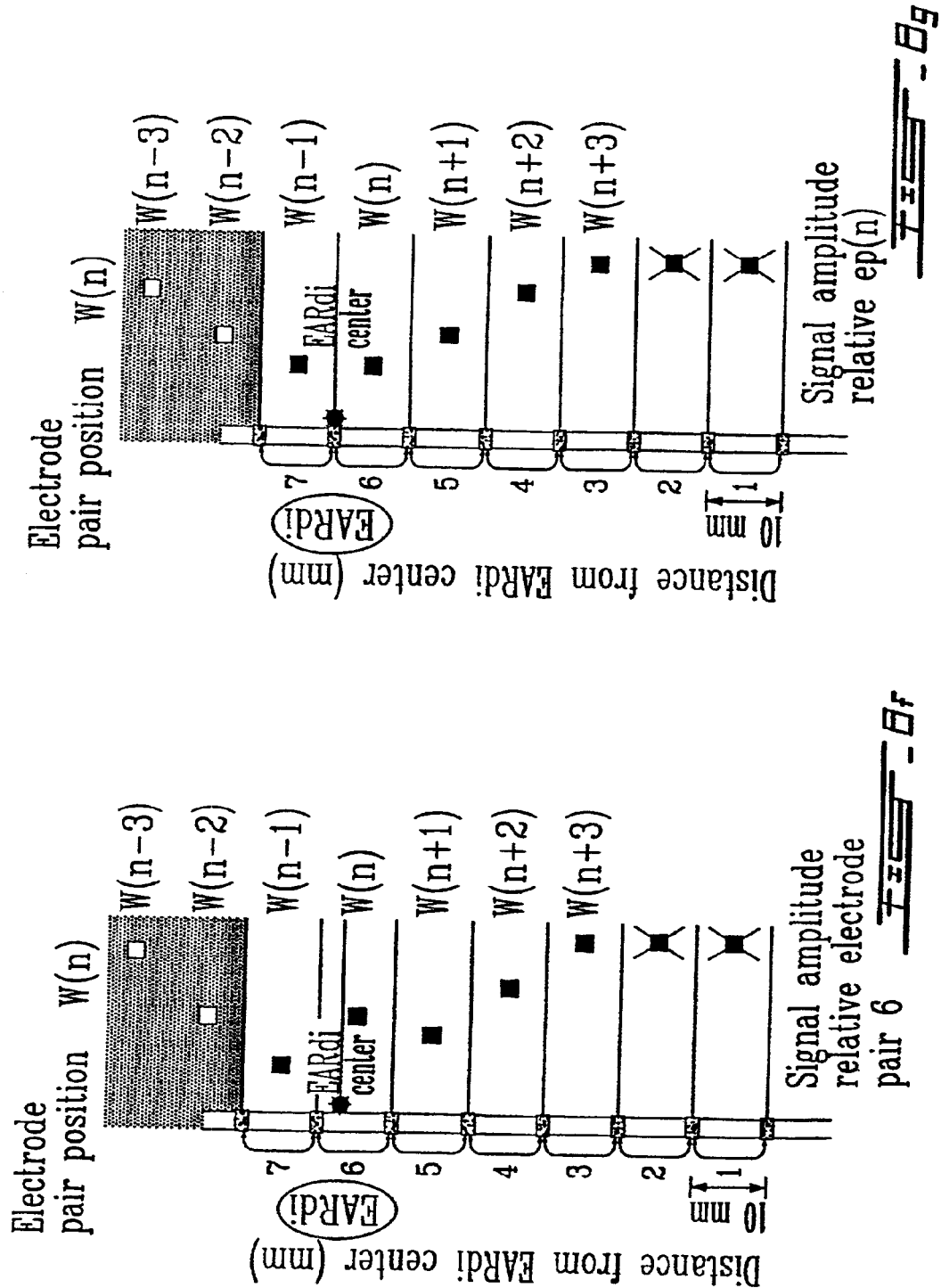

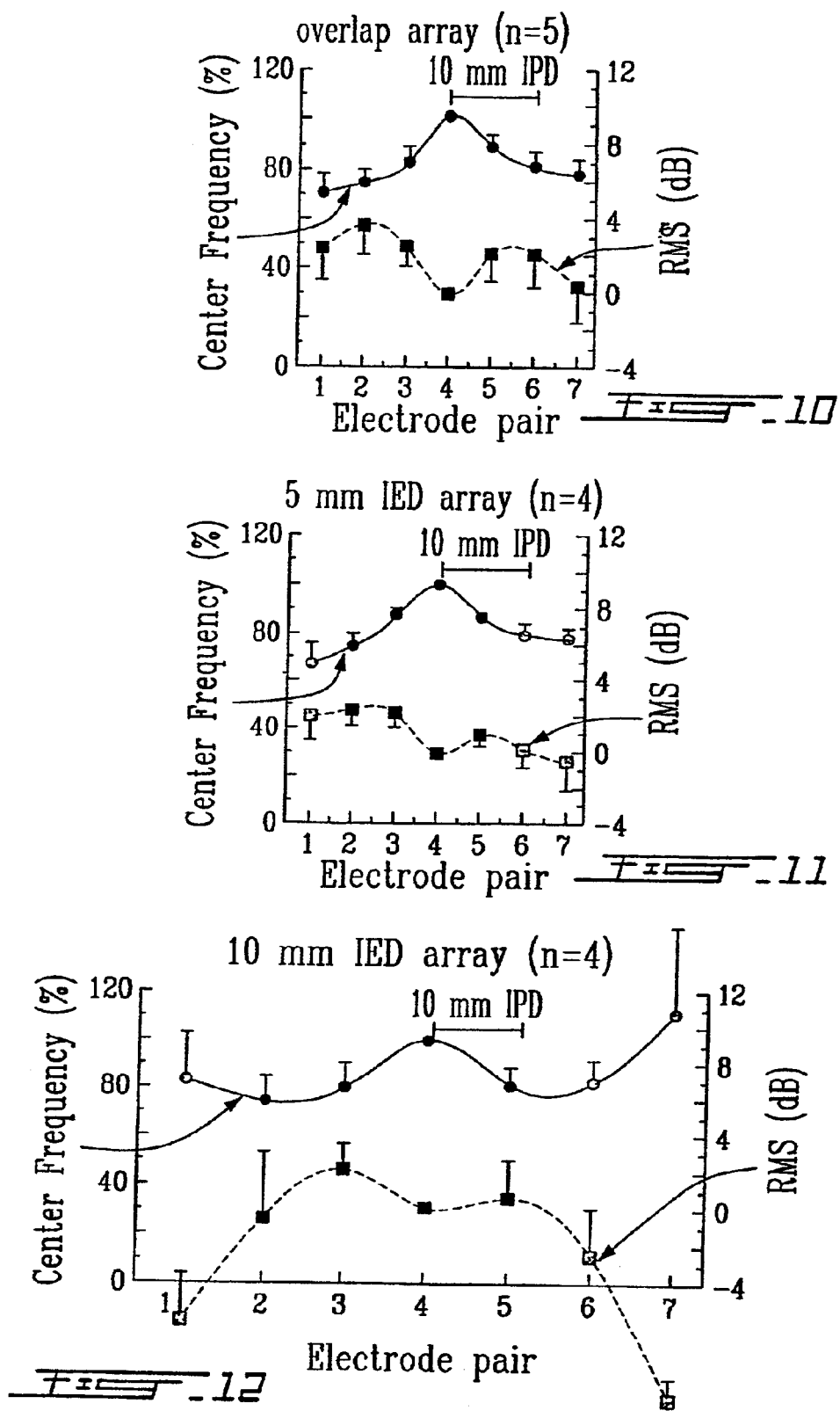

METHOD AND SYSTEM FOR PRODUCING A HIGHER QUALITY ELECTROMYOGRAPHIC SIGNAL FROM AN ELECTRODE ARRAY

This application claims the benefit of the earlier filed International Application No. PCT/CA00/00808, International Filing Date, 7 Jul. 2000, which designated the United States of America, and which international application was published under PCT Article 21(2) in English as WO Publication No. WO 01/03579 A1.

BACKGROUND OF THE INVENTION

1. Field of the Invention

The present invention relates to a method and system for producing a higher quality electromyographic signal from signals obtained with an array of electrodes, in which the electrode-sensed signals are corrected through implementation of a weighting function.

2. Brief Description of the Prior Art

The physiological mechanisms which generate myoelectrical activity when a muscle contracts have been known and understood for long time. In particular, how to record electromyographic signals from muscles through an array of electrodes is a well theoretically described topic in physiology.

Although the theoretical understanding is impressive, the bio-physiological application of this theory is, in practice, still partly deficient. As of today, there is known only one standardized and automatic processing system taking into consideration factors such as electrode filtering due to changes in the position of the array of electrodes relative to the center of the electrically active region of the muscle. Application of this technique includes limitations as to its adaptability to changes in inter-electrode distance and does not optimize the use of signals available along the electrode array with varying anatomy and inter-electrode distance.

Also, the prior art technology fails to provide for full correction of the signals obtained from electrodes of the array that are not symmetrically positioned with respect to the center of the electrically active region of the muscle.

OBJECTS OF THE INVENTION

An object of the present invention is therefore to overcome the above described drawback of the prior art by processing the electrode-sensed signals through a weighting function whose purpose is to correct these electrode-sensed signals for a distance separating the electrodes from the electrically active region of the muscle.

Another object of the present invention is to predict signals which cannot be measured through the array of electrodes.

SUMMARY OF THE INVENTION

More particularly, in accordance with the present invention, there is provided a method of producing a higher quality electromyographic signal describing myoelectrical activity of an electrically active region of a subjects muscle, comprising sensing through an array of electrodes a plurality of EMG (electromyogram) signals representative of the myoelectrical activity of the electrically active region of the subject's muscle, applying a weighting function to the detected EMG signals and thereby producing weighted signals wherein the weighting function contains correction features for the relative locations of the electrically active region and the electrodes, and combining the weighted signals and thereby producing the higher quality electromyographic signal.

The present invention further relates to a system for producing a higher quality electromyographic signal describing myoelectrical activity of an electrically active region of a subject's muscle, comprising an array of electrodes for sensing a plurality of EMG signals representative of the myoelectrical activity of the electrically active region of the subject's muscle, a weighting filter applied to the detected EMG signals to produce weighted signals wherein the weighting filter contains correction features for the relative locations of the electrically active region and the electrodes, and a combiner of the weighted signals wherein the combined weighted signals constitute the higher quality electromyographic signal.

In accordance with preferred embodiments of the present invention:

the electrically active region of the subject's muscle comprises a center, the electrodes are separated from the center of the electrically active region by respective distances, the electrodes are separated from each other by an inter-electrode distance, and the weighting function comprises correction features for:
  the relative location of the center of the electrically active region and the electrodes;
  the distance separating the center of the electrically active region and the electrodes;
  the size of the electrically active region; and
  the inter-electrode distance;
the weighting function comprises correction features for both cancellation and distance damping effects;
the electrically active region of the subject's muscle comprises a center, the array of electrodes comprises a series of electrodes with an inter-electrode distance, each EMG signal is detected through at least two electrodes of the array, and applying the weighting function comprises:
  detecting the position of the center of the electrically active region about the array of electrodes;
  relating the weighting function to the position of the center of the electrically active region with respect to the electrodes of the series;
  weighting each EMG signal by means of the weighting function related to the position of the center of the electrically active region with respect to the electrodes of the series;
the series of electrodes has a center and, when the center of the electrically active region is offset with respect to the center of the series of electrodes:
  a larger number of EMG signals are detected by the electrodes on one side of the center of the electrically active region than on the other side of that center of the electrically active region so that EMG signals are missing on the above mentioned other side; and
  weigthing of the EMG signals comprises replacing the missing EMG signals on the said other side by corresponding EMG signals from the said one side, and subsequently weighting the replacement EMG signals;
combining the weighted signals comprises adding a feature of the weighted signals together or calculating a mean of a feature of the weighted signals;
the method and system further comprise, prior to combining the weighted signals, evaluating electromyographic quality of the weighted signals;

evaluating electromyographic quality comprises applying to the weighted signals quality indexes for detection of at least one of the following parameters:
signal-to-noise ratio;
maximum-to-minimum drop in power density;
power spectrum deformation;
electrical activity related to electrocardiogram/esophageal peristalsis;

evaluating electromyographic quality comprises adding to each other two of the weighted signals detected through respective electrodes situated on opposite sides of the center of the electrically active region to produce a corresponding addition signal, subtracting these two weighted signals from each other to produce a corresponding subtraction signal, and comparing these addition and substration signals, this comparison being representative of the electromyographic quality of the weighted signals;

the method and system further comprise, prior to combining the weighted signals, replacing the weighted signals whose evaluated quality is insufficient; and the method and system comprise replacing the weighted signals whose evaluated quality is insufficient either by predicted values or by a last value of the weighted signals considered as containing electromyographic information; and the method and system comprise replacing the higher quality electromyographic signal in response to weighted signals of insufficient quality.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 1 is a schematic representation of a set-up of an EMG analysis system;

FIG. 2 is a section of oesophageal catheter on which an array of electrodes of the EMG analysis system of FIG. 1 is mounted;

FIG. 6 is a schematic diagram illustrating the concept embodied by the method and system according to the present invention;

FIG. 7 illustrates an exemplary weighting function related to the EMGdi signals collected through the array of electrodes of FIG. 2;

FIG. 8a is a first graph showing the gain values of a weighting function W(n) associated with the various pairs of electrodes of the array, when the center of the electrode array symmetrically overlies the EARdi center and the EARdi center is centered between a pair of electrodes;

FIG. 8b is a second graph showing the gain values of a weighting function W(n) associated with the various pairs of electrodes of the array, when the center of the electrode pair is shifted with respect to the EARdi center by a distance smaller than 0.5 inter-electrode distance, and the EARdi center is located between the electrodes of the central pair of the electrode array;

FIG. 8c is a third graph showing the gain values of a weighting function W(n) associated with the various pairs of electrodes of the array, when the center of the array is shifted with respect to the EARdi center by a distance equal to 0.5 inter-electrode distance and the EARdi center overlies an electrode common to both the central electrode pair and another adjacent electrode pair;

FIG. 8d is a fourth graph showing the gain values of a weighting function W(n) associated with the various pairs of electrodes of the array, when the center of the array is shifted with respect to the EARdi center by a distance between 0.5 and 1.5 inter-electrode distance;

FIG. 8e is a fifth graph showing the gain values of a weighting function W(n) associated with the various pairs of electrodes of the array, when the center of the array is shifted with respect to the EARdi center but the EARdi center is centered between a pair of electrodes as in FIG. 8a, and two missing EMGdi signals are predicted;

FIG. 8f is a sixth graph showing the gain values of a weighting function W(n) associated with the various pairs of electrodes of the array, when the center of the array is shifted with respect to the EARdi center by a distance smaller then 0.5 inter-electrode distance as in FIG. 8b, the EARdi center is located but not centered between a pair of electrodes, and two missing EMGdi signals are predicted;

FIG. 8g is a seventh graph showing the gain values of a weighting function W(n) associated with the various pairs of electrodes of the array, when the center of the array is shifted with respect to the EARdi center the EARdi center overlies an electrode of the array as in FIG. 8c, and two missing EMGdi signals are predicted;

FIG. 10 is another graph showing measured electrode filtering effects along an array of electrodes comprising overlapping pairs of electrodes;

FIG. 11 is a further graph showing measured electrode filtering effects along the array of electrodes of FIG. 2 for an inter-electrode distance of 5 mm; and FIG. 12 is still further a graph showing measured electrode filtering effects along the array of electrodes of FIG. 2 for an inter-electrode distance of 10 mm.

DETAILED DESCRIPTION OF THE PREFERRED EMBODIMENT

Figure 3:
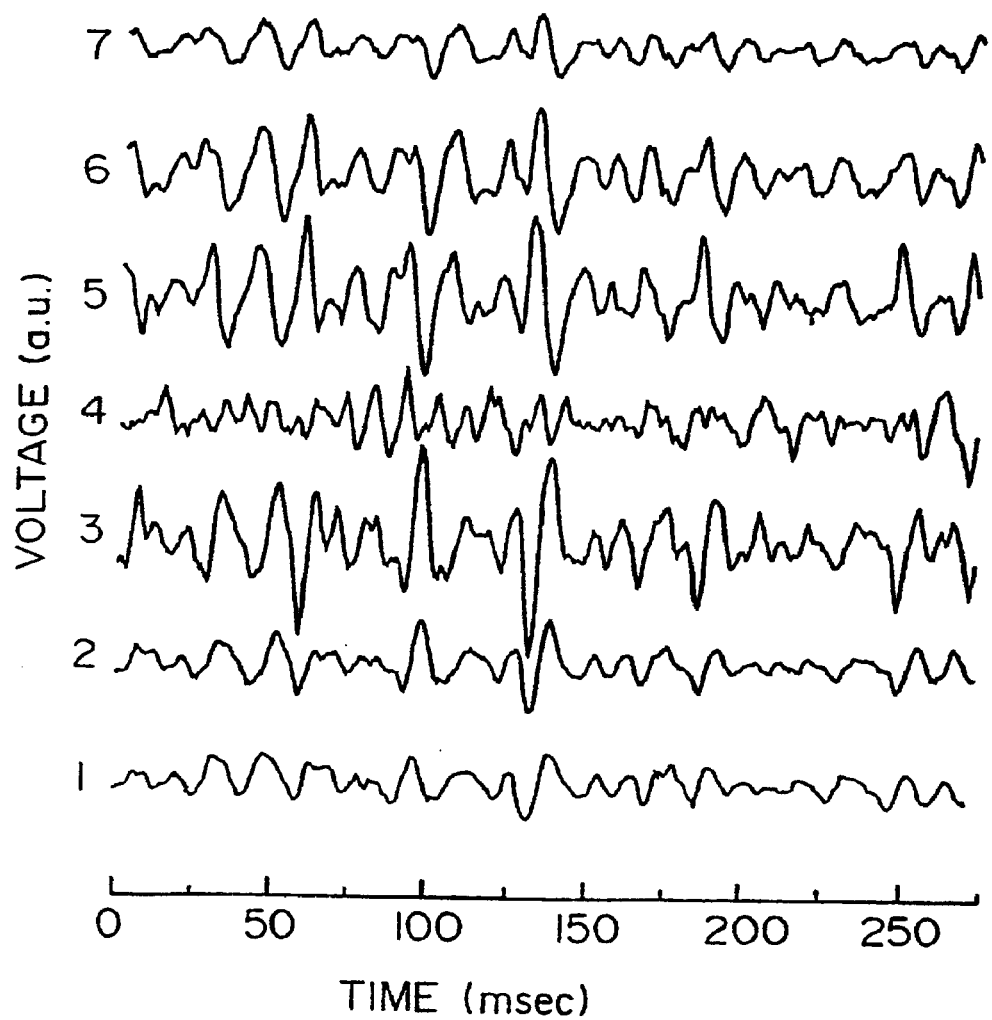
FIG. 3 is a graph showing a set of EMG signals of the diaphragm (EMGdi signals) detected by pairs of successive electrodes of the array of FIG. 2.

Electromyographic signals produced by a muscle can be detected by means of an array of electrodes passing through the center of the muscle electrically active region. The EMG signals detected through the electrodes comprise electromyographic and noise components, and the position of the center of the electrically active region of the muscle can be detected through a reversal of polarity of the electromyographic components of the electrode-sensed EMG signals provided that the polarity of the electrode pairs is consistent from one end to the other of the electrode array.

Although the preferred embodiment of the present invention will be described in relation to an electromyographic signal produced by the diaphragm of a subject, it should be kept in mind that it is within the scope of the present invention to process a signal representative of the myoelectrical activity of a muscle other than the diaphragm.

According to the preferred embodiment of the present invention, myoelectrical activity of the diaphragm 11 of a human subject 14 is measured through an array of electrodes such as 12 (FIGS. 1 and 2) mounted on the free end section 15 of an oesophageal catheter 13. As better illustrated in FIG. 2, the electrodes 12 are separated by an inter-electrode distance d. FIG. 1 shows that the catheter 13 is introduced into the subject's oesophagus through one nostril or the mouth until the array of electrodes 12 is situated at the level of the gastroesophageal junction.

An electrode 12 can be mounted on the free end section 15 of the catheter 13 by winding stainless steel wire (not shown) around that catheter 13. The wound stainless steel wire presents a rough surface smoothed out by solder, which in turn is electroplated with nickel, copper and then gold or silver. Of course, it is within the scope of the present invention to use other electrode structures. Also, the electrodes 12 can possibly be applied to a nasogastric feeding tube (not shown) which is routinely introduced in intensive-care unit (ICU) patients.

Electric wires (not shown) interconnect each pair of successive electrodes such as 1–7 (FIG. 2) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EMGdi signals (EMG signals from the diaghragm) collected by the various pairs 1–7 of electrodes 12 are shielded to reduce the influence of external noise, in particular disturbance from the 50 or 60 Hz current and voltage of the elecric mains.

The group of differential amplifiers 16 amplifies and bandpass fibers each EMGdi signal. This subtraction step can also be carried out in the personal computer 19 when the amplifiers 16 are single-ended or equivalently designed amplifiers (monopolar readings).

In the example illustrated in FIGS. 1 and 2, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that myoelectrical activity of the diaphragm can be measured accurately with an oesophageal catheter 13 provided on the free end section 15 thereof with an array of eight electrodes 12, a different number and/or configuration of pairs of electrodes 12 can be contemplated depending on the subject's anatomy and movement of the diaphragm. Also, the pairs 1–7 do not need to be pairs of successive electrodes; they can be overlapping pairs of electrodes or can present any other configuration of electrode pairs.

A major problem in recording EMGdi signals is to maintain the noise level as low and as constant as possible. Since the electric wires transmitting the EMGdi signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is preferably made as small as possible (miniaturized) and is positioned in close proximity to the subjects nose to decrease as much as possible the distance between the electrodes 12 and the amplifiers 16.

The amplified EMGdi signals are sampled by a personal computer 19 through respective isolation amplifiers of a unit 18, to form signal segments of fixed duration. Unit 18 supplies electric power to the various electronic components of the differential and isolation amplifiers while ensuring adequate isolation of the subject's body from such power supply. The unit 18 also incorporates bandpass filters included in the respective EMGdi signal channels to eliminate the effects of aliasing. The successive EMGdi signal segments are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 31.

It is believed to be within the capacity of those of ordinary skilled in the art to construct suitable differential amplifiers 16 and an adequate isolation amplifiers and power supply unit 18. Accordingly, the amplifiers 16 and the unit 18 will not be further described in the present specification.

An example of te seven EMGdi signals collected by the pairs 1–7 of successive electrodes 12 (FIGS. 1 and 2) and supplied to the computer 19 is illustrated in FIG. 3.

Step 401:

The first operation (step 401 of FIG. 4) performed by the computer 19 is a filtering operation to remove from all the EMGdi signals of FIG. 3 electrode motion artifacts, cardiac activity, electrical activity related to esophageal peristalsis, 50 and 60 Hz interference from the electric network, and high frequency noise. Implementation of such filtering is believed to be within the capacity of those of ordinary skill in the art and, accordingly, will not be further described.

Steps 402 and 403:

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array. Also the diaphragm moves during breathing and the method and system according to the invention accounts for this movement of the diaphragm.

The portion of the crural diaphragm 11 which forms the muscular tunnel through which the oesophageal catheter 13 is passed is referred to the "diaphragm electrically active region" (EARdi). The thickness of the EARdi is 20–30 mm. It can be assumed that, within the EARdi, the distribution of active muscle fibers has a center from which the majority of the EMGdi signals originate, i.e. the "diaphragm electrically active region center" (EARdi center). Therefore, when the polarity of the recordings is consistent from one end of the electrode array to the other, EMGdi signals detected on opposite sides of the EARdi center will be reversed in polarity with no phase shift; in other words, EMGdi signals obtained along the electrode array become reversed in polarity at the EARdi center.

Moving centrally from the boundaries of the EARdi, EMGdi power spectrums progressively attenuate and enhance in frequency. Reversal of signal polarity on either side of the electrode pair 4 with the most attenuated power spectrum confirms the position from which the EMGdi signals originate, the EARdi center.

Figure 4:
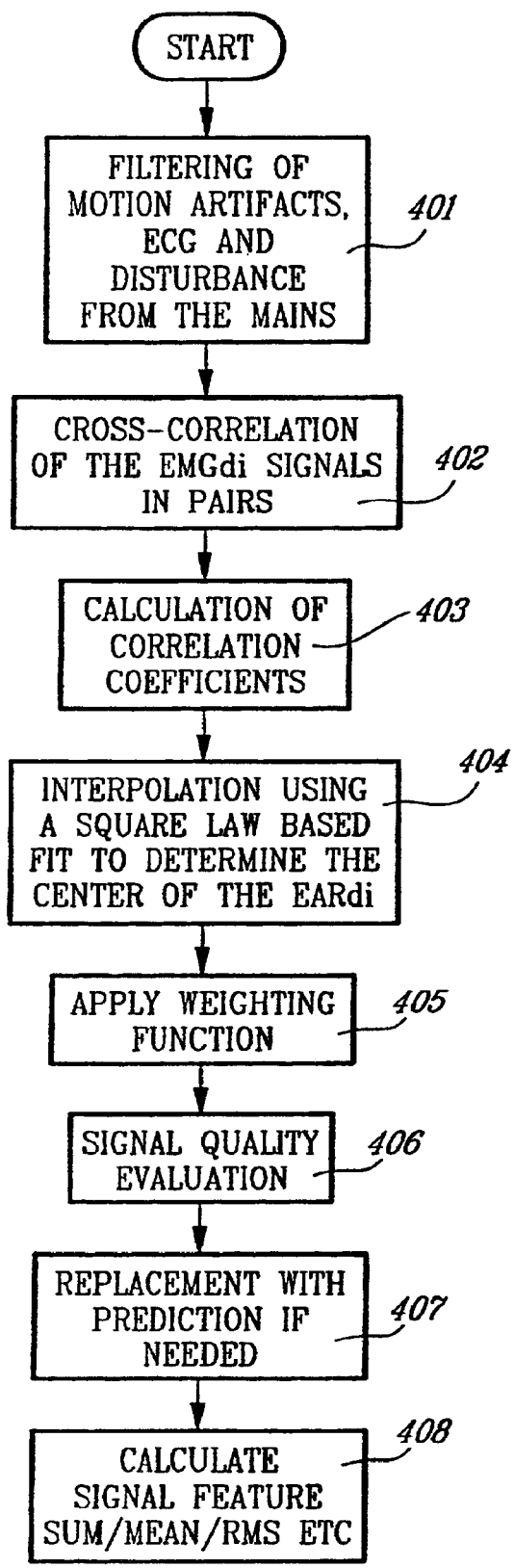
FIG. 4 is a flow chart illustrating the operation of a preferred embodiment of the method and system according to the invention, for producing a higher quality electromyographic signal describing the myoelectrical activity of a muscle.

Referring to FIG. 4, another function of the computer 19 is to determine the position of the EARdi center along the array of electrodes 12. The EARdi center is repeatedly updated, that is re-determined at predetermined time intervals.

For that purpose, the EMGdi signals are cross-correlated in pairs in step 402 to calculate cross-correlation coefficients r in step 403. As well known to those of ordinary skill in the art, cross-correlation is a statistical determination of the phase relationship between two signals and essentially calculates the similarity between two signals in terms of a correlation coefficient r. A negative correlation coefficient r indicates that the cross-correlated signals are of opposite polarities.

Figure 5:
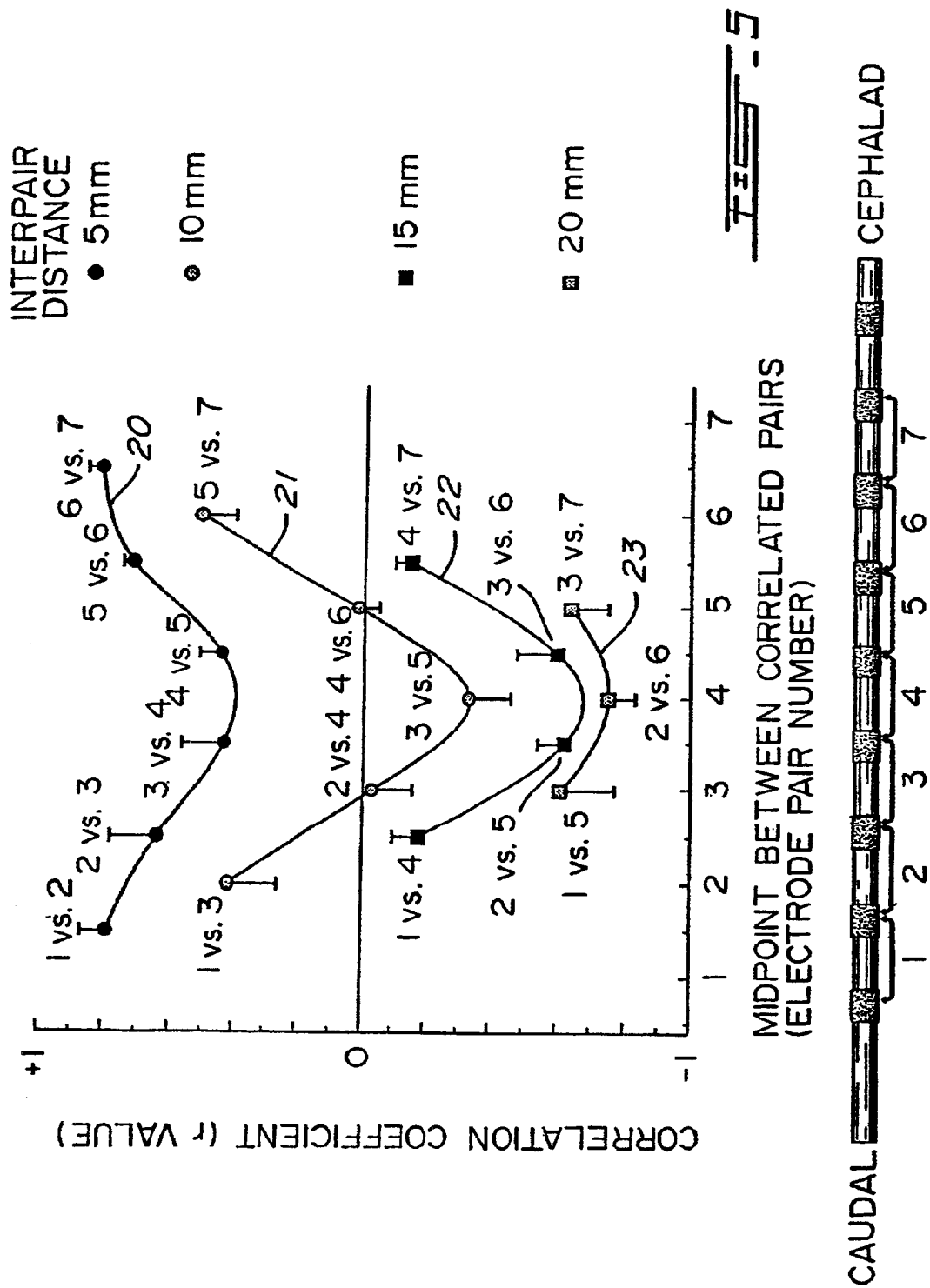
FIG. 5 is a graph showing the distribution of correlation coefficients calculated for determining the position of the center of an electrically active region (EARdi center) of the diaphragm of a subject along the array of electrodes of FIG. 2.

FIG. 5 shows curves of the value of the correlation coefficient r versus the midpoint between the pairs of electrodes from which the correlated EMGdi signals originate. In this example, the inter-electrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 5 that negative correlation coefficients r are obtained when EMGdi signals from respective electrode pairs situated on opposite sides of the electrode pair 4 are cross-correlated. It therefore appears that the change in polarity occurs in the region of electrode pair 4, which is confirmed by the curves of FIG. 3. Accordingly, it can be assumed that the EARdi center is situated substantially midway between the electrodes 12 forming pair 4.

Step 404:

In step 404, the correlation coefficients are systematically compared to determine the EARdi center. For example, the EARdi center can be precisely determined by interpolation using a square law based fit of the three most negative correlation coefficients of curve 21 obtained by successive cross-correlation of the EMGdi signal segments from each electrode pair to the EMGdi signal segments from the second next electrode pair. The EARdi center is associated to a pair of electrodes 12 to provide a "reference position". In the illustrated example, the EARdi center is associated to pair 4 of electrodes 12.

As mentioned in the foregoing description, the position of the EARdi center along the array of electrodes 12 is continuously updated, i.e. re-calculated at predetermined time intervals overlapping or not.

Step 405:

Each EMGdi signal obtained on either side of the EARdi center is processed, more specifically multiplied/divided/added/subtracted by a weighting function. More specifically, a given parameter of the EMGdi signal is multiplied/divided/added/subtracted by the weighting function. This given parameter may comprise a feature such as, for example, an amplitude, power, area under the rectified signal, etc.

The weighting function can be derived from a mathematical model capable of adjusting each EMGdi signal in relation to the relative position of the array of electrodes 12 with respect to the EARdi center. The weighting function can also be obtained from weighting-function-describing data measured on the subject's body, for example by measuring EMGdi signals along the electrode array with knowledge of the position of the EARdi center. Finally the weighting function can be derived from both the mathematical model and the weighting function describing data measured on the subject's body. Also, the processing can be performed in the time domain or in the frequency domain.

The weighting function contains correction for:

the relative location of the EARdi center with respect to the pairs of electrodes through which the EMGdi signals are obtained;

the distance separating the EARdi center from the electrodes;

the size of the electrically active region (EARdi) of the diaphragm; and the inter-electrode distance.

Knowing the position of the center of the electrically active region of the diaphragm (EARdi) about the array or electrodes, the mathematical model can produce weighting functions correcting for both cancellation effects and distance damping effects.

For the purpose of illustrating this concept, let's consider FIG. 6 in which wanted signals S from a wanted signal source 601 and disturbance signals D from disturbances 602 are detected through an array of electrodes 603. The array of electrodes comprises N electrodes labeled n, where n=1, 2, 3, 4 . . . N. The array of electrodes does not have to be linearly arranged; any configuration is possible.

The signal detected through a given electrode n depends on 1$^{st}$) the properties of the sources 601 and 602 (point sources or line sources with particular direction or curved line sources) and 2$^{nd}$) the distances $r_s(n)$ and $r_d(n)$, respectively, between the sources 601 and 602 and the electrode n. Line source signals display a mixed frequency and distance dependent damping essentially described by modified bessel functions while point source signals are damped inversely proportional to the distance and independent of frequency.

The signal from each electrode is processed through the weighting function W(n), which is a weighting filter which may be positive, negative or even equal to zero prior to a summation of all contributions (n=1 to N) to give the output signal.

The following relations describe signal conditioning in the spectral domain:

the signal u(n) at the given electrode n is $$u(n) = Sf_s[r_s(n)] + Df_d[r_d(n)] \qquad (1)$$

the output signal Out 604 is:

$$\text{Out} = \sum_{n=1}^{N} u(n) \, W(n) \qquad (2)$$

Combining the two equations and rearranging the terms give the following expression:

$$\text{Out} = S \sum_{n=1}^{N} f_s[r_s(n)] \, W(n) + D \sum_{n=1}^{N} f_d[r_d(n)] \, W(n) \qquad (3)$$

where $f_s$ and $f_d$ are functions describing damping and/or other alteration (such as interference) to the signal as a function of distances $r_s$ and $r_d$, respectively.

FIG. 7 is a graph illustrating an example of weighting function W(n). As can be seen the graph of FIG. 7 relates the weighting function W(n) to the position of the pairs of electrodes from which the EMGdi signals of FIG. 3 originate, and the center of the EARdi determined through the correlation coefficients r in steps 402–404.

In FIG. 7, curve 701 illustrating the weighting function W(n) shows that signals from electrode pairs 1, 2, 3, 4, 5, 6 and 7 are represented by respective local gain values of the weighting function W(n). The local gain values for all electrode pairs is determined by the position of the EARdi center along the array of electrodes. More specifically, the local gain value of electrode pair 4 is the gain value of curve 701 determined by the position of the EARdi center itself centered between the electrodes of pair 4 (see dashed line 702). The local gain value of electrode pairs 1, 2, 3, 5, 6 and 7 is the gain value of curve 701 at positions shifted from the EARdi center by a corresponding number of inter-electrode distances (see dashed lines 703–708). In the illustrated example, the signal from electrode pair 1 will be represented by gain value 0.05 (dashed line 703), the signal from electrode pair 2 will be represented by gain value 0.3 (dashed line 704), the signal from electrode pair 3 will be represented by gain value 0.9 (dashed line 705), the signal from electrode pair 4 will be represented by gain value 0.3 (dashed line 702), the signal from electrode pair 5 will be represented by gain value 0.9 (dashed line 706), the signal from electrode pair 6 will be represented by gain value 0.3 (dashed line 707), and the signal from electrode pair 7 will be represented by gain value 0.05 (dashed line 708).

In general terms, for a good performance, the first term of Equation 3 should be maximized and the second term minimized, or depending on the application of concern, known filtering strategies should be used to optimize the spectral distributions of wanted and disturbance signals. The optimization is performed by varying sign, strength, and spectral (complex) contents of the weighting filter W(n). This process can be guided by a priori knowledge of the type of signal source (line, point, etc.) and the corresponding type of damping (modified bessel functions, inverse distance damping, etc.) and/or experimental knowledge of the signals spectral content.

FIGS. 8a–8c are graphs showing the effect of moving the EARdi center along the array of electrodes from a position in which the EARdi center is located centrally between a pair of electrodes to a position in which the EARdi center overlies an electrode. These graphs clearly show how the signal amplitudes along the array of electrodes are affected by alteration of the position of the EARdi center with respect to the electrode pair 4.

The graph of FIG. 8a shows the gain values of the weighting function W(n) associated with the various pairs of electrodes of the array, when the center of the electrode array symmetrically overlies the EARdi center and the EARdi center is centered between the central electrode pair 4. The position of the EARdi center is the same as illustrated in FIG. 7. In FIG. 8a, electrode filtering is symmetrical and presents cancellation at electrode pair 4.

The graph of FIG. 8b illustrates the gain values of a weighting function W(n) associated with the various pairs of electrodes of the array, when the center of the array is shifted with respect to the EARdi center by a distance smaller than 0.5 inter-electrode distance. More specifically, in FIG. 8b, the EARdi center is moved (upwardly in the figure) by 25% of the inter-electrode distance. In this example, the weighting function is skewed, but there is still some cancellation at electrode pair 4.

FIG. 8c is a third graph showing the gain values of a weighting function W(n) associated with the various pairs of electrodes of the array, when the center of the array is shifted with respect to the EARdi center by a distance equal to 0.5 inter-electrode distance and the EARdi center is centered on an electrode. The resulting weighting function is symmetrical with no cancellation at electrode pair 4.

The above FIGS. 8a, 8b and 8c show three (3) possible locations of the EARdi center relative to an electrode pair centered on the electrode array. The fourth figure, namely FIG. 8d, exemplifies the behavior of the signals if the EARdi center continues to move over to an adjacent electrode pair. In this latter case, the gain values are the same as in FIG. 8b but are reversed.

FIGS. 8e, 8f and 8g show the same positional shifts as in FIGS. 8a, 8b and 8c but when the EARdi center is located at electrode pair 2 instead of central electrode pair 4. The EMGdi signals corresponding to weighting function gain values W(n+2) and W(n+3) then fall outside of the electrode array. The missing weighted signals can then be predicted by using the same EMGdi signal detected at electrode pairs 4 and 3 processed through the weighting function. These predicted values are then used in the calculation for the total signal strength across the electrode array.

In this preferred embodiment, the electrodes at the bottom of the army (FIGS. 8e–g) are not used. However, depending on how complex the model for prediction and computation is, these signals can also be used. If correction for signals that fall off the electrode array is not performed, it is impossible to obtain an accurate estimate of the total signal value.

Figure 9:
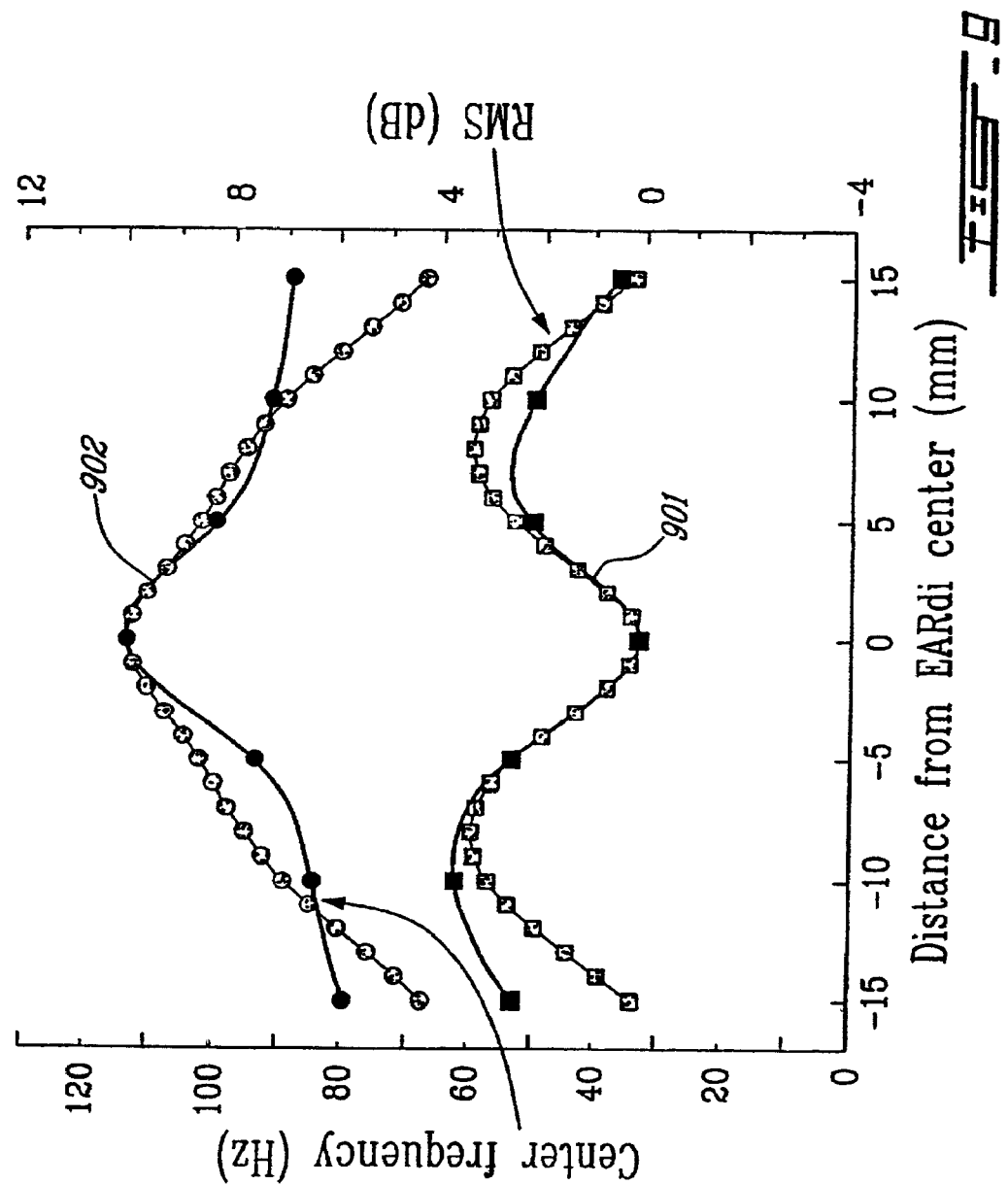
FIG. 9 is a graph showing measured and predicted electrode filtering effects along an array of electrodes such as that shown in FIG. 2.

Just a word to mention that the weighting function W(n) of the FIGS. 7 and 8 regards conditioning of the amplitude of the EMGdi signal and corresponds to curve 901 of FIG. 9 (curve of the amplitude of the EMGdi signal in relation to the distance of the electrodes of the pair from the EARdi center). The EMGdi signals can also be frequency conditioned by constructing a weighting filter using a curve such as 902 in FIG. 9 (curve of the center frequency of the EMGdi signal in relation to the distance of the electrodes of the pair from the EARdi center). A combination of frequency and amplitude conditioning can also be implemented.

FIGS. 10, 11 and 12 are other examples of amplitude and frequency conditioning curves that can serve as weighting functions W(n).

The curves of FIGS. 9, 10, 11 and 12 are usually experimentally established on a sufficient number of recordings in a subject.

Step 406:

In this step, electromyographic quality of the weighted signals is evaluated.

This evaluation of the electromyographic quality of all the weighted signals can be performed for their relative electromyographic and noise components. Thus, if preferred, summation of the EMGdi signals (amplitude, area under the curve, power, etc.) along the array of electrodes can be limited to signals that contain physiological information pertaining to the diaphragm. This evaluation of signals content can be performed by applying well known signal quality indexes for detection of signal-to-noise ratio, maximum-to-minimum drop in power density, power spectrum deformation, and/or electrocardiogram/esophageal peristalsis.

This evaluation of signals for their relative electromyographic and noise components can also be obtained by adding and subtracting EMGdi signals obtained on opposite sides with symmetrical position to the electrically active region center (for example signals from electrode pairs 3 and 5 in FIG. 7) and comparing the results of these addition and subtraction. A first EMGdi signal detected by a pair of electrodes of the array on a first side of the center of the EARdi has an electromyographic component of a first polarity and a noise component of given polarity. A second EMGdi signal detected by another pair of electrodes of the array on the second side of the EARdi center, opposite to the first side, has an electromyographic component of a second polarity opposite to the first polarity and a noise component of said given polarity. Subtraction of the first and second EMGdi signals subtracts the noise components of the first and second EMGdi signals from each other but adds the electromyographic components of these first and second EMGdi signals together to produce a resulting signal with high electromyographic content and low noise content.

Addition of the first and second EMGdi signals adds the noise components of the first and second EMGdi signals to each other but subtracts the electromyographic components of these first and second EMGdi signals from each other to produce a signal with low electromyographic content and high noise content. Comparison of the resulting added and subtracted signals (area under the curve/power/amplitude of the signals) provides information about the relative contribution of noise and electromyographic content to the signal. Signals with a high electromyographic content will be considered as a high quality signal.

Step 407:

EMGdi signals considered as not containing physiological information (insufficient quality as determined in step 406) pertaining to the diaphragm can be replaced by predicted values or simply the last value considered to contain physiological information pertaining to the diaphragm. This replacement strategy can be applied on either each single EMGdi signal obtained from the electrode array or on the summation or mean of the weighted EMGdi signals representative for all or some of the signals obtained along the electrode array.

Step 408:

The last step consists of calculating the sum of a feature (RMS voltage, RMS current, power, RMS means amplitude, area under the curve, etc) of the eventually replaced, signal quality evaluated weighted EMGdi signals from the electrodes of the array. A mean of the rectified signals, or a RMS or other suitable or equivalent value of these signals can be calculated as well for further use.

The resulting signal will provide improvement of the signal-to-noise ratio and minimize influence of electrode filtering due to changes in the position of the electrode array relative the muscle's electrically active region center. It also accounts for differences in anatomy between individuals and differences in inter-electrode distance and design, and for the EARdi center approaching the distal or proximal end of the array of electrodes.

Of course, the application of the present invention is not limited to the diaphragm but to any other muscle and that, for any type of array of electrodes.

Although the present invention has been described hereinabove by way of a preferred embodiment thereof, this embodiment can be modified at will, within the scope of the appended claims, without departing from the spirit and nature of the subject invention.

What is claimed is:

1. A method of producing a higher quality electromyographic signal describing myoelectrical activity of an electrically active region of a subject's muscle, comprising:
   sensing through an array of electrodes a plurality of EMG signals representative of the myoelectrical activity of the electrically active region of the subject's muscle;
   applying a weighting function to the detected EMG signals and thereby producing weighted signals, the electrically active region of the subject's muscle comprising a center and the weighting function containing correction features for the relative locations of the center of the electrically active region and the electrodes; and
   combining the weighted signals and thereby producing the higher quality electromyographic signal.

2. A method of producing a higher quality electromyographic signal as defined in claim 1, wherein the weighting function comprises correction features for both cancellation and distance damping effects.

3. A method of producing a higher quality electromyographic signal as defined in claim 1, wherein combining the weighted signals comprises:
adding a feature of the weighted signals together.

4. A method of producing a higher quality electromyographic signal describing myoelectrical activity of an electrically active region of a subject's muscle, comprising:
   sensing through an array of electrodes a plurality of EMG signals representative of the myoelectrical activity of the electrically active region of the subject's muscle;
   applying a weighting function to the detected EMG signals and thereby producing weighted signals; and
   combining the weighted signals and thereby producing the higher quality electromyographic signal;
wherein:
   the electrically active region of the subject's muscle comprises a center;
   the electrodes are separated from the center of the electrically active region by respective distances;
   the electrodes are separated from each other by an inter-electrode distance; and
   the weighting function comprises correction features for:
      the relative location of the center of the electrically active region and the electrodes;
      the distance separating the center of the electrically active region and the electrodes;
      the size of the electrically active region; and
      the inter-electrode distance.

5. A method of producing a higher quality electromyographic signal describing myoelectrical activity of an electrically active region of a subject's muscle, comprising:
   sensing through an array of electrodes a plurality of EMG signals representative of the myoelectrical activity of the electrically active region of the subject's muscle;
   applying a weighting function to the detected EMG signals and thereby producing weighted signals, the weighting function containing correction features for the relative locations of the electrically active region and the electrodes; and
   combining the weighted signals and thereby producing the higher quality electromyographic signal;
   wherein the electrically active region of the subject's muscle comprises a center, the array of electrodes comprises a series of electrodes with an inter-electrode distance, each EMG signal is detected through at least two electrodes of the array, and wherein applying the weighting function comprises:
      detecting the position of the center of the electrically active region about the array of electrodes;
      relating the weighting function to the position of the center of the electrically active region with respect to the electrodes of said series;
      weighting each EMG signal by means of the weighting function related to the position of the center of the electrically active region with respect to the electrodes of said series.

6. A method of producing a higher quality electromyographic signal as defined in claim 5, wherein the series of electrodes has a center, and wherein, when the center of the electrically active region is offset with respect to the center of the series of electrodes:
   a larger number of EMG signals are detected by the electrodes on one side of the center of the electrically active region than on the other side of said center of the electrically active region so that EMG signals are missing on said other side; and
   weigthing of the EMG signals comprises replacing the missing EMG signals on said other side by corresponding EMG signals from said one side and subsequently weighting said replacement EMG signals.

7. A method of producing a higher quality electromyographic signal describing myoelectrical activity of an electrically active region of a subject's muscle, comprising:

sensing through an array of electrodes a plurality of EMG signals representative of the myoelectrical activity of the electrically active region of the subject's muscle;

applying a weighting function to the detected EMG signals and thereby producing weighted signals, the weighting function containing correction features for the relative locations of the electrically active region and the electrodes; and combining the weighted signals and thereby producing the higher quality electromyographic signal, wherein combining the weighted signals comprises calculating a mean of a feature of the weighted signals.

8. A method of producing a higher quality electromyographic signal describing myoelectrical activity of an electrically active region of a subject's muscle, comprising:

sensing through an array of electrodes a plurality of EMG signals representative of the myoelectrical activity of the electrically active region of the subject's muscle;

applying a weighting function to the detected EMG signals and thereby producing weighted signals, the weighting function containing correction features for the relative locations of the electrically active region and the electrodes; and combining the weighted signals and thereby producing the higher quality electromyographic signal;

wherein said method of producing a higher quality electromyographic signal further comprises, prior to combining the weighted signals, evaluating electromyographic quality of the weighted signals.

9. A method of producing a higher quality electromyographic signal as recited in claim 8, wherein evaluating electromyographic quality comprises applying to the weighted signals quality indexes for detection of at least one of the following parameters:

signal-to-noise ratio;

maximum-to-minimum drop in power density;

power spectrum deformation;

electrical activity related to electrocardiogram/esophageal peristalsis.

10. A method of producing a higher quality electromyographic signal as recited in claim 8, wherein the electrically active region of the subject's muscle comprises a center, and wherein evaluating electromyographic quality comprises adding to each other two of the weighted signals detected through respective electrodes situated on opposite sides of the center of the electrically active region to produce a corresponding addition signal, subtracting said two weighted signals from each other to produce a corresponding subtraction signal, and comparing said addition and subtraction signals, said comparison being representative of the electromyographic quality of the weighted signals.

11. A method of producing a higher quality electromyographic signal as recited in claim 8, further comprising, prior to combining the weighted signals, replacing the weighted signals whose evaluated quality is insufficient.

12. A method of producing a higher quality electromyographic signal as recited in claim 11, comprising replacing the weighted signals whose evaluated quality is insufficient by predicted values.

13. A method of producing a higher quality electromyographic signal as recited in claim 11, comprising replacing the weighted signals whose evaluated quality is insufficient by a last value of said weighted signals considered as containing electromyographic information.

14. A method of producing a higher quality electromyographic signal as recited in claim 8, comprising replacing the higher quality electromyographic signal in response to weighted signals of insufficient quality.

15. A system for producing a higher quality electromyographic signal describing myoelectrical activity of an electrically active region of a subject's muscle, comprising:

an array of electrodes for sensing a plurality of EMG signals representative of the myoelectrical activity of the electrically active region of the subject's muscle;

a weighting filter applied to the detected EMG signals to produce weighted signals, the electrically active region of the subject's muscle comprising a center and the weighting filter containing correction features for the relative locations of the center of the electrically active region and the electrodes; and a combiner of the weighted signals, the combined weighted signals constituting the higher quality electromyographic signal.

16. A system for producing a higher quality electromyographic signal as defined in claim 15, wherein the weighting filter comprises correction features for both cancellation and distance damping effects.

17. A system for producing a higher quality electromyographic signal describing myoelectrical activity of an electrically active region of a subject's muscle, comprising:

an array of electrodes for sensing a plurality of EMG signals representative of the myoelectrical activity of the electrically active region of the subject's muscle;

a weighting filter applied to the detected EMG signals to produce weighted signals, the weighting filter containing correction features for the relative locations of the electrically active region and the electrodes; and a combiner of the weighted signals, the combined weighted signals constituting the higher quality electromyographic signal;

wherein: the electrically active region of the subject's muscle comprises a center;

the electrodes are separated from the center of the electrically active region by respective distances;

the electrodes are separated from each other by an inter-electrode distance; and the weighting filter comprises correction features for:

the relative location of the center of the electrically active region and the electrodes;

the distance separating the center of the electrically active region and the electrodes;

the size of the electrically active region; and the inter-electrode distance.

18. A system for producing a higher quality electromyographic signal describing myoelectrical activity of an electrically active region of a subject's muscle, comprising:

an array of electrodes for sensing a plurality of EMG signals representative of the myoelectrical activity of the electrically active region of the subject's muscle;

a weighting filter applied to the detected EMG signals to produce weighted signals, the weighting filter containing correction features for the relative locations of the electrically active region and the electrodes; and a combiner of the weighted signals, the combined weighted signals constituting the higher quality electromyographic signal;

wherein:
the electrically active region of the subject's muscle comprises a center;
the array of electrodes comprises a series of electrodes with an inter-electrode distance;
each EMG signal is detected through at least two electrodes of the array; and
the weighting filter comprises a weighting function related to the position of the center of the electrically active region with respect to the electrodes of said series.

19. A system for producing a higher quality electromyographic signal describing myoelectrical activity of an electrically active region of a subject's muscle, comprising:
an array of electrodes for sensing a plurality of EMG signals representative of the myoelectrical activity of the electrically active region of the subject's muscle;
a weighting filter applied to the detected EMG signals to produce weighted signals, the weighting filter containing correction features for the relative locations of the electrically active region and the electrodes; and
a combiner of the weighted signals, the combined weighted signals constituting the higher quality electromyographic signal;
wherein the series of electrodes has a center, wherein the electrically active region of the subject's muscle has a center, and wherein, when the center of the electrically active region is offset with respect to the center of the series of electrodes:
a larger number of EMG signals are detected by the electrodes on one side of the center of the electrically active region than on the other side of said center of the electrically active region so that EMG signals are missing on said other side; and
the system comprises means for replacing the missing EMG signals on said other side by corresponding EMG signals from said one side, and means for subsequently weighting said replacement EMG signals.

20. A system for producing a higher quality electromyographic signal describing myoelectrical activity of an electrically active region of a subject's muscle, comprising:
an array of electrodes for sensing a plurality of EMG signals representative of the myoelectrical activity of the electrically active region of the subject's muscle;
a weighting filter applied to the detected EMG signals to produce weighted signals, the weighting filter containing correction features for the relative locations of the electrically active region and the electrodes; and
a combiner of the weighted signals, the combined weighted signals constituting the higher quality electromyographic signal;
wherein the combiner comprises:
an adder of a feature of the weighted signals.

21. A system for producing a higher quality electromyographic signal describing myoelectrical activity of an electrically active region of a subject's muscle, comprising:
an array of electrodes for sensing a plurality of EMG signals representative of the myoelectrical activity of the electrically active region of the subject's muscle;
a weighting filter applied to the detected EMG signals to produce weighted signals, the weighting filter containing correction features for the relative locations of the electrically active region and the electrodes; and
a combiner of the weighted signals, the combined weighted signals constituting the higher quality electromyographic signal;
wherein the combiner comprises:
a calculator of a mean of a feature of the weighted signals.

22. A system for producing a higher quality electromyographic signal describing myoelectrical activity of an electrically active region of a subject's muscle, comprising:
an array of electrodes for sensing a plurality of EMG signals representative of the myoelectrical activity of the electrically active region of the subject's muscle;
a weighting filter applied to the detected EMG signals to produce weighted signals, the weighting filter containing correction features for the relative locations of the electrically active region and the electrodes; and
a combiner of the weighted signals, the combined weighted signals constituting the higher quality electromyographic signal;
wherein said system for producing a higher quality electromyographic signal further comprises, prior to combining the weighted signals, an evaluator of an electromyographic quality of the weighted signals.

23. A system for producing a higher quality electromyographic signal as recited in claim 22, wherein the evaluator comprises means for applying to the weighted signals quality indexes for detection of at least one of the following parameters:
signal-to-noise ratio;
maximum-to-minimum drop in power density;
power spectrum deformation;
electrical activity related to electrocardiogram/esophageal peristalsis.

24. A system for producing a higher quality electromyographic signal as recited in claim 22, wherein the electrically active region of the subject's muscle comprises a center, and wherein the evaluator comprises an adder of two of the weighted signals detected through respective electrodes situated on opposite sides of the center of the electrically active region to produce a corresponding addition signal, a subtractor of said two weighted signals from each other to produce a corresponding subtraction signal, and a comparator of said addition and subtraction signals, this comparison being representative of the electromyographic quality of the weighted signals.

25. A system for producing a higher quality electromyographic signal as recited in claim 22, further comprising means for replacing, prior to combining the weighted signals, the weighted signals whose evaluated quality is insufficient.

26. A system for producing a higher quality electromyographic signal as recited in claim 25, comprising means for replacing the weighted signals whose evaluated quality is insufficient by predicted values.

27. A system for producing a higher quality electromyographic signal as recited in claim 25, comprising means for replacing the weighted signals whose evaluated quality is insufficient by a last value of said weighted signals considered as containing electromyographic information.

28. A system for producing a higher quality electromyographic signal as recited in claim 22, comprising means for replacing the higher quality electromyographic signal in response to weighted signals of insufficient quality.

* * * * *